US00PP14132P39

(12) United States Plant Patent
Anderson, III et al.

(10) Patent No.: US PP14,132 P3
(45) Date of Patent: Sep. 16, 2003

(54) PISTACHIO ROOTSTOCK NAMED 'PN 15-4'

(76) Inventors: Henry P. Anderson, III, 1021 E. Cartmill, Tulare, CA (US) 93274; Kenneth L. Puryear, 5911 W. Prospect Dr., Visalia, CA (US) 93291

( * ) Notice: Subject to any disclaimer, the term of this patent is extended or adjusted under 35 U.S.C. 154(b) by 0 days.

(21) Appl. No.: 10/035,680

(22) Filed: Dec. 28, 2001

(65) Prior Publication Data

US 2003/0126653 P1 Jul. 3, 2003

(51) Int. Cl.[7] ..... A01H 5/00
(52) U.S. Cl. ..... Plt./152
(58) Field of Search ..... Plt./152

(56) References Cited

U.S. PATENT DOCUMENTS

PP4,953 P 11/1982 Anderson et al.
PP4,994 P 3/1983 Anderson et al.

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new and distinct variety of pistachio tree, characterized by the deep, dark red color of young foliage, the rich dark green color of mature foliage, and the rounded upright growth habit in young trees.

3 Drawing Sheets

CLASSIFICATION

The present invention relates to a new Pistachio plant.

VARIETY DENOMINATION

The new Pistachio plant has the varietal denomination 'PN 15-4'.

BACKGROUND OF THE INVENTION

The present invention relates to a new and distinct variety of pistachio tree, which is a hybrid formed from the crossing of *Pistachio atlantica* as seed parent with *P. integerrima* as pollen parent.

The male parent *P. atlantica* has the following characteristics: Leaves are pinnately compound of eleven and sometimes less, with leaflets nearly opposite, lanceolate and sessile. Leaflets are small, leathery and semi gloss to matte. Margins of leaflets are entire with alternate and pinnate venation pattern. Leaflet color is dark green on topside and lighter green on bottom side when mature. Immature leaflets are green with reddish tint. Rachis and center rib of leaflets slightly lighter color green than rest of leaf surface. Leaf surface is glabrous. The length of leaves including petioles averages 4.09 inches and averages 2.75 inches to end of rachis. Individual leaflets average 1.36 inches long and 0.485 inches wide at widest point. Average rachis length is 2.07 inches. Petiole length averages 0.71 inches and has an average diameter of 0.065 inches. Entire leaf width averages 2.73 inches. Leaves without petiole average 3.50 inches in length. Main branches of tree are rough in nature and brownish with limbs smoother and a grayish brown. Limbs have small red marks running opposite of the grain.

The female parent *P. integerrima* has the following characteristics: Leaves are pinnately compound of nine and sometimes less with leaflets nearly opposite, lanceolate and sessile. Leaflets are medium small, leathery semi gloss to matte. Margins of leaflets are entire with an alternate and pinnate venation pattern. Leaflet color is medium to dark green on topside with slightly lighter green on bottom side when mature. Immature leaflets are red. Rachis and center rib of leaflets are slightly lighter green than rest of leaf surface. Leaf surface is glabrous. The length of leaves including petiole averages 10.78 inches and averages 7.9 inches to end of rachis. Individual leaflets average 4.09 inches long and 1.65 inches wide at widest point. Average rachis length is 3.91 inches. Petiole length averages 2.46 inches and average diameter of 0.124 inches. Entire leaf width averages 8.3 inches. Main branches of trees are smooth and grayish brown with limbs also smooth and gray and absent of red marks.

SUMMARY OF THE INVENTION

The 'PN 15-4' variety is characterized by small, leathery leaves, with new glossy leaflets and older leaflets that are semi-glossy to dull. New leaflets are a deep, dark red and the older leaflets are rich, dark green. Centers of newer leaves are red and centers of older leaves are reddish green.

Growth of the variety is rounded and upright when young. The trunk is generally round, and mature growth is light brown in color, while new growth is reddish. Vegetative buds are small and reddish on new growth and larger reddish brown on older growth.

The 'PN 15-4' variety differs from its parents in the following characteristics:

1. Leaf and leaflet size: The male parent's leaves and individual leaflets are considerably smaller than that of 'PN 15-4', while the female parent's leaves and individual leaflet size are larger.

2. Leaflet color: Male and female parent leaflets are a lighter green color than that of 'PN 15-4', which has a rich dark green color.

3. Petiole and rachis color: Both male and female parents have light green rachis and petiole whereas 'PN 15-4' has a deep red petiole and rachis.

4. Rachis and Petiole sizes: The male parent's rachis and petiole are considerably smaller than that of 'PN 15-4', while the female parent's rachis and petiole are considerably larger.

The variety is particularly useful as a rootstock upon which commercial nut bearing pistachio varieties may be budded or grafted.

Asexual reproduction by budding onto *P. integerrima* at Kern County, Calif. shows that the foregoing and other distinguishing characteristics come true to form and are established and transmitted through succeeding propagation. Other known forms of asexual reproduction for pistachios may also be employed.

BRIEF DESCRIPTION OF ILLUSTRATIONS

The accompanying photographic illustrations show typical specimens of vegetative growth of the new variety, in color as nearly true as it is reasonably possible to make in a color illustration of this character.

DESCRIPTION OF THE NEW VARIETY

Referring now specifically to the new and distinct variety of pistachio tree, the following is a detailed description of one year old plants with color description where indicated by reference to *The Royal Horticultural Society Colour Chart,* except where common terms of color definition are employed.

The new variety of pistachio tree as herein described may vary in slight detail due to climatic, soil and cultural conditions under which the variety may be grown, the present description being of the variety as grown at Kern County, Calif.

Figure 1:
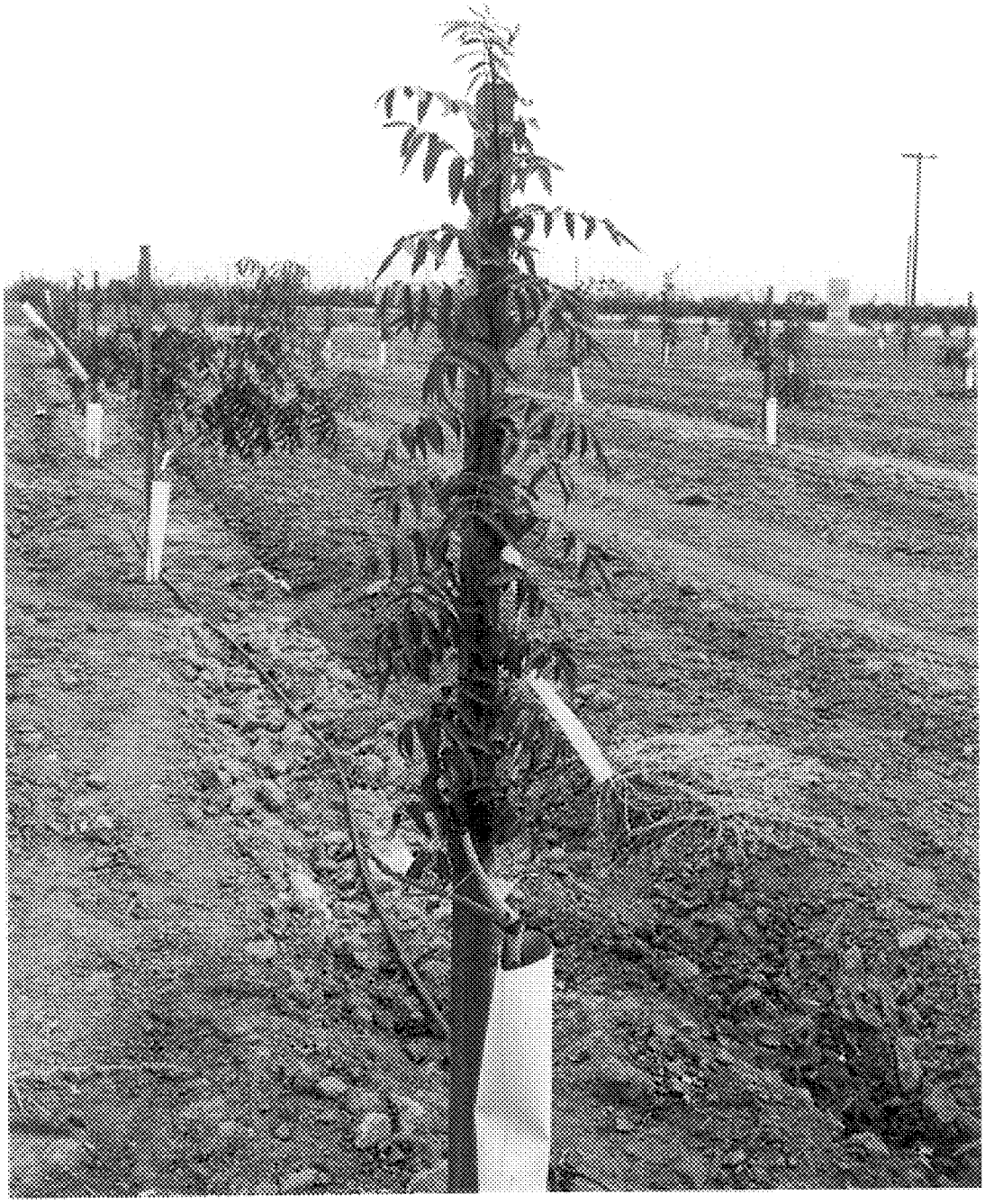
FIG. 1 shows a one year old pistachio tree of the new variety.
Figure 2:
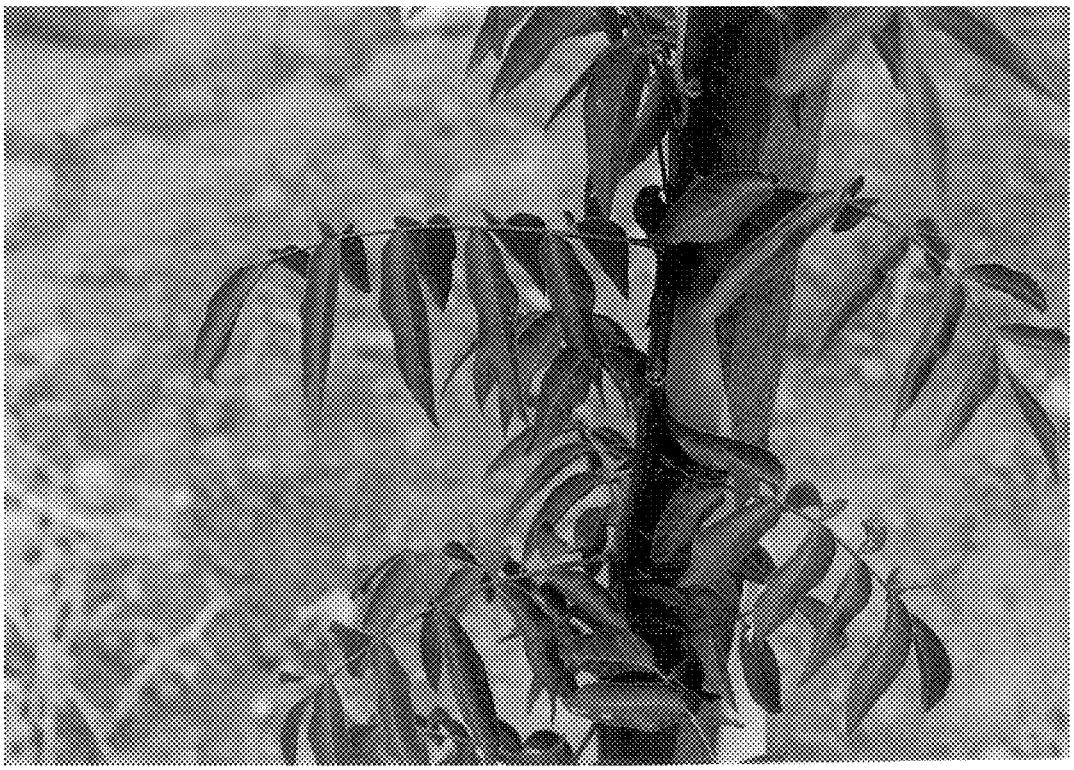
FIG. 2 shows a close-up of the trunk and compound leaves, typically with eleven leaflets.

Foliage:

*Leaves*.—Compound of eleven (sometimes less), as indicated in FIG. 2.

Figure 3:
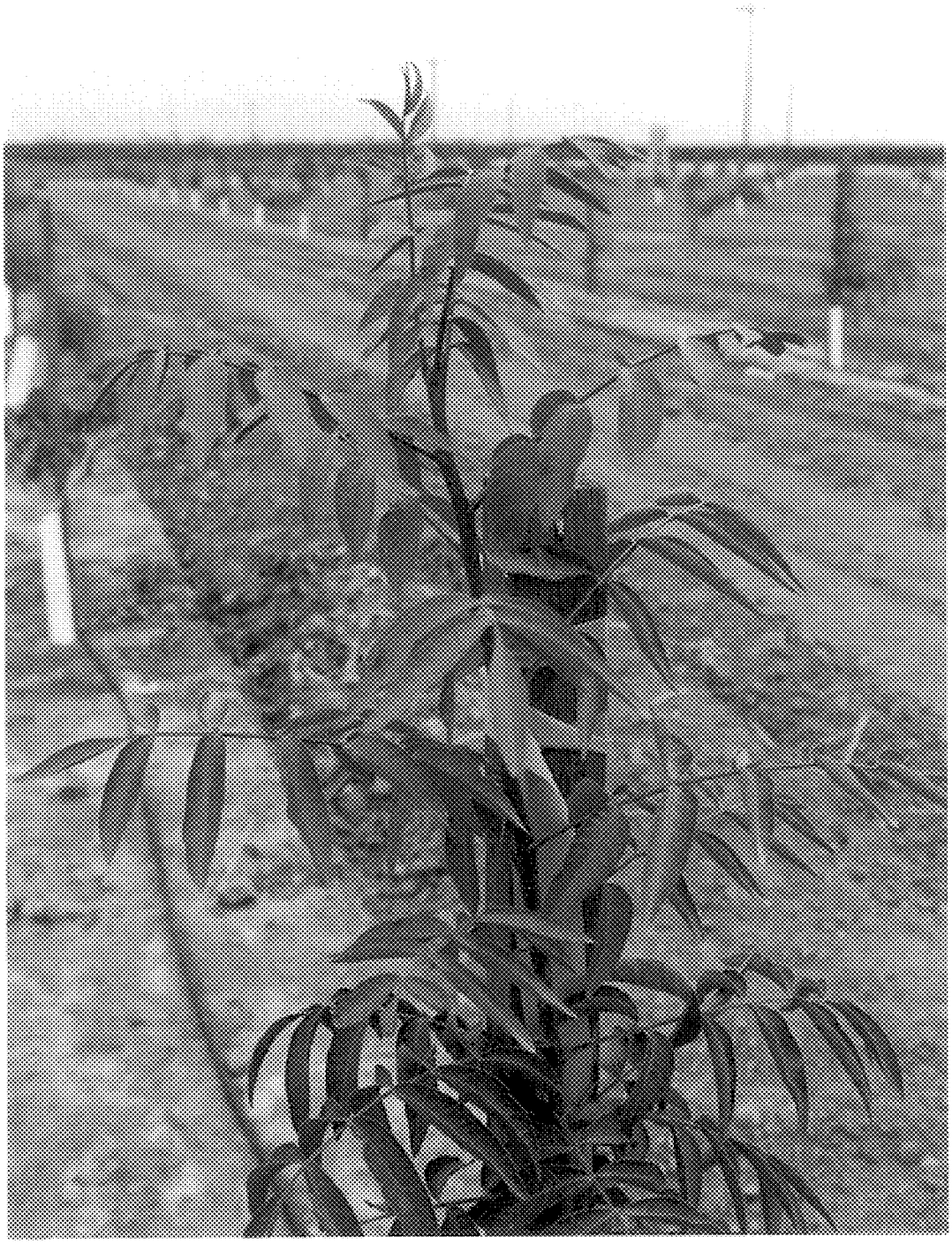
FIG. 3 shows a close-up of the new variety with both dark red new leaflets and dark green older leaflets.

*Leaflets*.—Small, leathery, with new leaflets glossy and older leaflets semi glossy to dull. Shape: medium length and narrow (lanceolate) apex acute, base acute but less so than apex. Color: new leaflets a deep dark red, near Greyed-red Group 178A, with older leaflets a rich dark green, near Greyed-green Group 189A, as shown in FIG. 3. Ribs: (Centers) on leaves are red, near Greyed-red Group 178B, in newer leaves to reddish green, near Greyed-red Group 181B, in mature leaves. In mature leaves, the center rib of leaflets and the leaflet veins are lighter green, near Greyed-green Group 189C, than the leaflets. In newer leaves, the center rib of the leaflet and the leaflet veins are lighter red, near Greyed-red Group 182C, than the leaflets.

*Length of leaves* (*including petiole and leaflets*).—May average about 8 inches and about 5.5 inches to end of midrib. Individual leaflets may average up to about 3 inches. The length of the leaf of the observed plant including petiole and leaflets averages 8.32 inches.

*Leaf arrangement*.—Pinnately compound with eleven leaflets, sometimes less, nearly opposite, lanceolate and sessile. The margins of the leaflets are entire. Apex of leaflets are acute. Base of leaf cuneate.

*Leaflet*.—The observed plant has an entire margin and a pinnate and alternate venation pattern. The length of leaflet averages 2.94 inches and averages 0.98 inches in width at the widest point on the leaflet. The leaflet has a leathery characteristic on top of the leaflet with a smoother surface on bottom. Leaf surface is glabrous. The color of the new leaflets is deep dark red on both sides, while the mature leaflets turn a deep dark green on top with a lighter green on bottom.

*Rachis*.—Averages 4.18 inches in length with deep red in young tissue, turning lighter red to reddish green in older tissue.

*Petiole*.—The petiole length of the observed plant averages 1.32 inches with a diameter of 0.118 inches. The color of the petiole is a deep dark red in both immature and mature tissue.

Growth:

*Habit*.—Rounded and upright when young.

*Trunk*.—Trunk is rounded. Light brown in color, near Greyed-orange Group 175A, on older growth and deep red, near Greyed-red Group 178A,in newer growth. Vegetative buds are small and reddish on new growth with larger reddish brown buds on older growth. The trunk diameter of the observed plant is 1.42 inches taken from 13.9 inches above ground level on a two-year-old tree. Bark texture is rough. The bark is light brown with darker brown markings running up the grain with small reddish markings running across the grain.

We claim:

1. A new and distinct variety of pistachio tree, identified as 'PN 15-4,' substantially as shown and described.

* * * * *